United States Patent
Brown et al.

(10) Patent No.: US 6,667,047 B2
(45) Date of Patent: *Dec. 23, 2003

(54) ULTRA-STABLE COMPOSITION COMPRISING MORINGA OIL AND ITS DERIVATIVES AND USES THEREOF

(75) Inventors: James H. Brown, Scottsdale, AZ (US); Robert Kleiman, Mesa, AZ (US); John C. Hill, Mesa, AZ (US)

(73) Assignee: International Flute Technologies LTD, Gilbert, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/964,988

(22) Filed: Sep. 26, 2001

(65) Prior Publication Data

US 2003/0113391 A1 Jun. 19, 2003

Related U.S. Application Data

(63) Continuation-in-part of application No. 09/917,091, filed on Jul. 27, 2001, now Pat. No. 6,528,075.

(51) Int. Cl.[7] ............................. A61K 7/00; A61K 7/04; A61K 7/021; A61K 7/025; A61K 7/06

(52) U.S. Cl. ........................... 424/401; 424/61; 424/63; 424/64; 424/70.1

(58) Field of Search ................................. 424/401, 776, 424/63, 64, 61, 70.1; 514/844, 867

(56) References Cited

U.S. PATENT DOCUMENTS 5,660,865 A * 8/1997 Pedersen et al. .............. 426/99

* cited by examiner

Primary Examiner—Thurman K Page
Assistant Examiner—Humera N. Sheikh
(74) Attorney, Agent, or Firm—The Halvorson Law Firm

(57) ABSTRACT

Cosmetic compositions with enhanced slip and/or break strength are described, said compositions comprising ultra-stable moringa oils, or its derivatives. These compositions may be used in cosmetic applications such as creams, lotions, and liquid foundations; massage oils; pressed products, such as eye shadow, blush, and powder; molded products, such as lipstick, lip balm, foundation, blush, eye liner, eye shadow, mascara; and hair care products, such as leave in conditioners, relaxers, hair dyes and other applications. The oils derived from the moringa plant should have a percent methylene interrupted unsaturation of less than 1%. The compositions may have at least one supplemental additive, such as malic acid, kojic acid, or ascorbic acid, present in an amount of from 0.01 to 2% or more by weight of the composition and the tocopherol is present in an amount of from 0.01 to 5% by weight of the composition.

25 Claims, No Drawings

ULTRA-STABLE COMPOSITION COMPRISING MORINGA OIL AND ITS DERIVATIVES AND USES THEREOF

This application is a continuation-in-part of application Ser. No. 09/917,091, which was filed on Jul. 27, 2001 now U.S. Pat. No. 6,528,075.

FIELD OF THE INVENTION

The present invention relates to emollients, particularly emollients used in conjunction with cosmetic and pharmaceutical products that are externally applied to patients. The present invention particularly relates to the provision of oxidatively stable emollients produced from moringa oil or its derivatives.

BACKGROUND

Emollients are materials that are applied to the skin of subjects to produce softness or smoothness. They have been used for centuries in both cosmetic and pharmaceutical products. The original emollients were extracts or directly concentrated materials from plants or animals, while modern emollients also include partially synthetic (derivatives of natural products) or completely synthetic materials. The natural emollients, for the most part, have tended to provide a wet or oily feel and appearance to the skin of humans. The synthetic and partially synthetic emollients have been tailored to provide the specific type of appearance and feel desired in an end product. Even with this tailoring, there are only a few synthetic emollients that provide a highly satisfactory dry feel. Silicon emollients are the most successful dry-feel emollients.

In recent years there has been an increasing attempt in many commercial fields to use natural products from renewable sources or at least naturally derived products. In part this effort has been through use of natural biodegradable materials that require a minimum amount of processing initiated to help reduce pollution of the environment. Silicones tend to be a class of synthetic material that is not easily degraded by the environment. The trend towards the use of natural biodegradable products in cosmetics provides motivation for manufacturers and compounders to seek alternatives to even the more successful synthetic components of their products, including silicon emollients.

In addition to the feel of an emollient, cosmetics and their ingredients must exhibit stability, both in storage and in use. The cosmetics must not deteriorate or separate in storage and use, and the individual ingredients should not decompose or otherwise undergo chemical changes that alter their desirable properties. One of the more common susceptibilities of products or components to ambient damage is from oxidation, and natural materials are clearly, through observation, susceptible to oxidation, as is commonly seen by browning of fruit exposed to air or the rancid smell of old vegetable oils. Many foods, food additives, cosmetics, fragrances, medicaments, and colorants are well known to be subject to damaging effects from oxidation.

The most frequent means of reducing the effects of oxidation (including light amplified or stimulated oxidation) include oxygen excluding packaging (e.g., bottles, cans, oxygen impermeable polymer wraps, and the like.), chemical modifications of the ingredient to reduce its tendency toward oxidation while minimally altering its functional properties, and the addition of antioxidants to directly quench oxidative species before they oxidize the ingredient. Packaging controls are most effective where a product is to be used once, as when the package is opened, air is introduced into the container and the package provides no complete protection against contact with oxygen. Chemical modification of an ingredient offers more general protection, assuming that a modification can be devised that both substantially reduces the tendency towards oxidation and also maintains the functional properties desired in the selection of the underlying chemical. This can be an exhaustive task, with no guarantees of success.

The use of antioxidants offers a general approach to the oxidation problem for a wide variety of materials and fields including the protection of edible materials against premature oxidation. The use of antioxidants would appear to some to require little more than the appropriate selection of an antioxidant sold commercially for specific purposes to achieve a commercially viable product with a necessary level of oxidation resistance. However, antioxidants may have and often display unique interaction with other ingredients and with the primary component on either a physical level (by not blending with the other materials), on a chemical level by reaction with active ingredients, or both. It is therefore necessary, with some compositions that require antioxidant protection, to conduct extensive research with no assurance of success. There are also such a wide variety of classes of antioxidants and so many variants within the classes that a search for an appropriate antioxidant is a highly problematic search, and the desire for the best antioxidant assures a time consuming process.

Among the more common classes of antioxidants are free-radical terminators, particularly those with available hydrogens from phenolic hydroxyl groups. Within that single class are the subclasses of butylated hydroxyanisole (BHA) and butylated hydroxytoluene (BHT), hydroquinones (such as tertiary-butylhydroquinones, propyl gallate, and tocopherols). Reducing agents or oxygen scavengers encompass another class of antioxidants and includes ascorbic acid (vitamin C) and its derivatives (such as esters of ascorbic acid, such as ascorbyl palmitate); sulfites (such as sulfur sulfite, alkali metal sulfites, and bisulfites, including alkali metal bisulfites); glucose oxidase (including catalse); erythrobic acid and its derivatives. Chelating agents comprise another class of materials that have been used to address problems with potentiators of oxidation and include citric acid (and its derivatives), polyphospages, and aminopolycarboxylic acids (such as ethylenediaminetetraacetic acid (EDTA). Finally, there are other antioxidant classes with less general areas of use.

The use of polyglycerol esters as oil in water (o/w) emulsifiers for cosmetic formulations is described, for example, in J. Soc. Cosmet. Chem. 28, 733–740 (1977) and in Fette, Seifen, Anstrichmettel 88, 101–106 (1986). In addition, the use of selected polyglycerol fatty acid esters as cosmetic emulsifiers is claimed in DE-A1 40 05 819 and DE-A1 40 23 593 (BASF). However, in cases where the esters based on unsaturated or saturated fatty acids mentioned in these documents are used, it has been found that the resulting emulsions are not always sufficiently stable in storage and/or are low in viscosity, i.e. have a viscosity that is not sufficiently high, so that problem-free dosing is difficult. The invention of that reference relates to cosmetic and/or pharmaceutical formulations that are characterized in that they contain statistical monoesters of technical triglycerol with saturated $C_{16}$–$C_{18}$ fatty acids as emulsifiers, the monoester content being from 30–50% by weight. It was asserted that it was surprising that the degree of self-condensation of the oligoglycrols in conjunction with the nature of the fatty acid and the percentage content of monoesters has a critical bearing on the properties of the resulting emulsifiers. That invention includes in particular the observation that the establishment of a percentage monoester content of 30–50% in the emulsifiers according to the invention leads to a significant improvement in storability and viscosity compared with otherwise known products of the prior art.

The Moringa family reportedly consists of approximately 10–14 Xerophytic species distributed from tropical Africa to the East Indies. Several species exist including *Moringa concanensis, Moringa oleifera, Moringa drouhardii* and *Moringa peregrina*.

Interest in the oil extracted from *M. oleifera*, known commercially as 'Ben' or 'Behen' oil, has existed for well over a century. In 1817 a petition containing particulars relating to the oil from *M. oleifera* was presented to the Jamaican House of Assembly. The petition described the oil as being useful for salads and culinary purposes and to be equal to the best Florence oil as an illuminant giving a clear light without smoke. A subsequent paper presented to the Jamaica Society of Arts in 1854 described how samples of oil had been tested by two watch making establishments in Kingston and had been reported to be equal to the expensively imported 'watch oil'. Subsequent reports indicated that the oil was used extensively as a lubricant until being replaced by sperm-whale oil. The oil was said to have unique properties being able to resist becoming rancid. However, this is not the case, the oil will eventually turn rancid—as indeed will all vegetable oils. The oil has also been reported to have been used extensively in the 'enfleurage' process whereby delicate fragrances are extracted from flower petals. There are references to the current use of the oil in the cosmetic industry and to its use for culinary purposes, however, there is no evidence to support this.

The first recorded study of the composition of the oil was carried out in 1848, which revealed a fatty acid with a high melting point. This was subsequently called behenic acid from which the commercial name for *M. oleifera* oil came. Over the years a number of different studies have been carried out to determine the composition and characteristics of the oil. The oil produced is pale yellow in color, non-drying with a mild, characteristic nutty flavor. The seed kernel contains on average 35% by weight oil, the fatty acid composition of that has been determined in a number of studies. The table below provides details obtained from the most recent of these. The variation in composition and quantity of the individual fatty acids arises primarily from differences in the variety of seed analyzed and the analytical techniques used.

TABLE 1

Summary of recent fatty acid analyses

| | | Composition % | | | |
|---|---|---|---|---|---|
| Fatty Acid | | Ferrao and Ferrao (1970) | Dahot and Memon (1985) | NRI (1993) | TEI (1995) |
| Myristic | C14:0 | — | 1.4 | 0.1 | — |
| Palmitic | C16:0 | 6.7 | 3.5 | 5.9 | 6.9 |
| Palmitoleic | C16:1 | — | — | 1.1 | 1.1 |
| Stearic | C18:0 | 4.3 | 8.3 | 5.1 | 8.3 |
| Oleic | C18:1 | 76.5 | 67.3 | 72.9 | 67.7 |
| Linoleic | C18:2 | 0.7 | 3.5 | 0.6 | 0.4 |
| Linolenic | C18:3 | — | — | 0.1 | — |
| Arachidic | C20:0 | 2.7 | 2.7 | 3.6 | 4.7 |
| Eicosenoic | C20:1 | — | — | 2.3 | 2.6 |

TABLE 1-continued

Summary of recent fatty acid analyses

| | | Composition % | | | |
|---|---|---|---|---|---|
| Fatty Acid | | Ferrao and Ferrao (1970) | Dahot and Memon (1985) | NRI (1993) | TEI (1995) |
| Behenic | C22:0 | 4.6 | 5.6 | 7.3 | 7.4 |
| Lignoceric | C24:0 | 1.1 | 3.2 | 1.0 | 0.4 |

As the table shows, the fatty acid composition is considered to be similar to that for olive oil and as such suitable is considered suitable for edible purposes. More recently the oil has also been shown to be particularly effective in the manufacture of soap producing a stable lather with high washing efficiency.

The presscake obtained following oil extraction may be utilized as a fertilizer. Its use as a potential animal feed has, in the past, not been recommended as it contains an alkaloid and a saponin. Work is currently being carried out to verify this and, if necessary, to determine suitable methods for detoxification. A recent finding has been that the presscake still contains the active fractions that may be utilized as a water treatment chemical.

Juice from fresh moringa leaves can be used to produce an effective plant growth hormone, increasing yields by 25–30% for nearly any crop: onions, bell pepper, soya, maize, sorghum, coffee, tea, chili, melon, etc. One of the active substances is Zeatin, a plant hormone from the Cytokinines group. This foliar spray should be used in addition to (and not in lieu of) other fertilizers, watering and sound agricultural practices. In one trial, use of this spray increased maize yields from 60 to 130 sacks per hectare.

Using moringa as a green manure can significantly enrich agricultural land. In this process, the land is first tilled. Moringa seed is then planted 1–2 cm deep at a spacing of 10×10 cm (a density of one million seed per hectare). The density can be greater. The only limits to plant density are availability of seed, water and fertilizer. After 25 days, the seedlings are plowed into the soil to a depth of 15 cm. The land is prepared again for the crop desired. Seeding can be done mechanically if the seed is first de-hulled.

Moringa leaves can be used as cattle feed (beef and milk cows), swine feed, and poultry feed. With moringa leaves constituting 40–50% of feed, milk yields for dairy cows and daily weight gains for beef cattle increased 30%. Birth weight, averaging 22 kg for local Jersey cattle, increased by 3–5 kg.

There are reports of moringa being used in cosmetic preparations as far back as 1400 BC, wherein an allegedly successful remedy to treat wrinkles consisted of: gum of frankincense wax; fresh moringa oil; Cyprus grass. The mixture was ground finely, mixed with fermented plant juice, and applied daily. In modem cosmetic products, moringa oil can be used effectively in skin- and hair care products as a stable emollient with a pleasant skin feel and special fragrance-fixing properties.

SUMMARY OF INVENTION

It is an object of the present invention to provide a composition having high slip characteristic comprising a long-chain oil of moringa, said long-chain oil has a methylene interrupted unsaturation of less than 1%, where the long-chain oil of moringa has a slip value greater than that of castor oil.

It is another object of the present invention that the long-chain oils of the above composition is a derivative of the oil produced from moringa.

It is yet another object of the present invention wherein said composition above is used in cosmetic applications selected from the group consisting of creams, lotions, and liquid foundations; massage oils; pressed products, such as eye shadow, blush, and powder; molded products, such as lipstick, lip balm, foundation, blush, eye liner, eye shadow, mascara; and hair care products, such as leave in conditioners, relaxers, hair dyes and other applications where there is a need for slip characteristics.

It is a further object of the present invention to provide an improved binder for inclusion into cosmetic formulation comprising a long-chain oil of moringa, said long-chain oil has a methylene interrupted unsaturation of less than 1%, where the inclusion of said binder into a cosmetic formulation provides a greater break strength relative to a standard formulation.

It is yet a further object of the present invention that the long-chain oil above is a derivative of the oil produced from moringa.

It is still yet a further object of the present invention to provide an improved binder composition is used in cosmetic applications selected from the group consisting of creams, lotions, and liquid foundations; massage oils; pressed products, such as eye shadow, blush, and powder; molded products, such as lipstick, lip balm, foundation, blush, eye liner, eye shadow, mascara; and hair care products, such as leave in conditioners, relaxers, hair dyes and other applications where there is need for a binder in the formulation.

It is another object of the present application to provide a composition for solid phase cosmetic formulations comprising a long-chain oil of moringa, said long-chain oil has a methylene interrupted unsaturation of less than 1%, where the long-chain oil of moringa has a slip value greater than that of castor oil and a greater break strength relative to a standard formulation.

It is yet another object of the present invention that the long-chain oils above is a derivative of the oil produced from moringa.

It is still yet another object of the present invention to provide a composition for solid phase cosmetic formulations wherein said cosmetic formulation is creams, lotions, and liquid foundations; massage oils; pressed products, such as eye shadow, blush, and powder; molded products, such as lipstick, lip balm, foundation, blush, eye liner, eye shadow, mascara; and hair care products, such as leave in conditioners, relaxers, hair dyes or other applications where there is need for high slip and improved break strength.

It is a further object of the present invention to provide a massage oil having improved slip properties comprising a long-chain oil of moringa, said long-chain oil has a methylene interrupted unsaturation of less than 1%, where the long-chain oil of moringa has a slip value greater than that of castor oil.

It is yet a further object of the present invention that the long-chain oil above is a derivative of the oil produced from moringa.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DETAILED DESCRIPTION OF PREFERRED EMBODIMENTS

Compositions or fluids comprising oils or waxes derived from the moringa plant, bean, seed and/or nut can be provided with a surprisingly large increase in oxidation stability by their combination with mixtures of particular classes of antioxidants, particularly the combination with at least a tocopherol. The stabilization combination, according to the present invention, is particularly effective when the long-chain organic molecules comprising moringa oil having less than 1% methylene interrupted polyunsaturation. Even more surprising is the dramatically large increase in oxidation stability when a supplemental additive selected from the group comprising malic acid, kojic acid, and ascorbic acid, is further included into the combination. The tocopherol is preferably present in an amount of from 0.01 to 5% by weight of the composition and the at least one supplemental additive is preferably present in an amount of from 0.01 to 2% or more by weight of the composition.

Described herein, by way of example of the inventive composition, is an emollient that is comprised of oil, or derivatives hereof, produced from the moringa plant in combination with an oxidation stabilizing system comprising at least one tocopherol. The emollient using the composition of the present invention is oxidatively ultra-stable relative to emollient compositions that do not include the oxidation stabilizing system of the present invention. Preferably, the oils, and their derivatives, produced from the moringa plant should have a percent methylene interrupted unsaturation of less than 1%. Herein, the term "long-chain oil of moringa" includes pure moringa oil and derivatives thereof. Herein, "derivatives" of moringa oil means oils produced from the moringa plant that are further processed to create such as moringa oil methyl ester, moringa oil ethyl ester, moringa oil isopropyl ester, hydrogenated moringa oil, and the like.

Ethyl esters of oils, particularly from triglyceride oils are commercially available from a number of different sources and are available from many different natural material sources, such as for example: Kukui Nut (*Aleurites molucunna*) oil ethyl ester; Borage seed oil (*Borago officinalis*) ethyl ester; Hazelnut (*Corylus avellana*) oil; Sweet Almond oil; Apricot kernel oil; the ethyl ester of arachidonic acid (5,8,11,14-Eicosatetraenoic acid ethyl ester); Avacado ethyl ester (ethyl perseate); ethyl esters of isostearic acid, lactic acid, lauric acid, myrisic acid, stearic acid, palmitic acid (hexadecanoic acid), ricinoleic acid (12-hydroxy-9-octadecanoic acid), and linoleic acid; Mink oil ethyl ester (ethyl mustelate); olive oil ethyl ester (ethyl olivoleate); ethyl ximenynate (ethyl santalbate); *Silybum marianum* ethyl ester (derived from *Silybum marianum* oil); and the like. These ethyl esters are readily manufactured from the base oils by conventional reactions with ethanol (preferably anhydrous ethyl alcohol) and an esterification catalyst. Many of these oils, and their ethyl esters, are primarily indicated as skin-conditioning agents and/or emollients with the individual esters varying in their chemical characteristics, substituent groups, molecular weights, and degrees of methylene interrupted unsaturation. However, these materials have been found to have their oxidative stability dramatically shortened by the ethyl esterification.

The characteristic of the degree of methylene interrupted unsaturation has some particular significance for the selection of preferred materials in the practice of the present invention, with moringa oils, and their derivatives, having less than 1% methylene interrupted unsaturation being most desirable. The term "percent methylene interrupted unsaturation" is used as a description of the internal structure of these various components of the oils, such as triglycerols and esters. The term literally means the weight percent of acyl groups having double bonds separated by or interrupted by a methylene group, —$CH_2$—. This term is used to better explain the reactivity of fatty acyl groups whose double bonds are so far away from one another that they behave chemically as monoenoic fatty acyl groups. For example, consider the double bonds at the delta-5 and delta-13 position of meadowfoam oil. The double bonds are so remote from each other that the acyl group acts as if it were monoenoic. The two double bonds do not interact in a way that would cause the fatty acid group to behave as a dienoic molecule rather than as a monoenoic molecule. The weight percent of acyl groups having double bonds separated by a methylene group is calculated, then added to other such acyl groups to determine the total percent methylene interrupted unsaturation. Soybean oil, for example, has two such acyl groups, linoleic and linolenic acids. The weight percentages of these two acyl groups in soybean oil are usually 52% and 6%, respectively. The percent methylene interrupted unsaturation is therefore 58%.

All oils, and their derivatives, oxidatively degrade. Their oxidative stability is measured and compared using an oxidative stability index (OSI, as outlined in The Official and Tentative Methods of the American Oil Chemists' Society, AOCS Method Cd12b-92). Use of the most common antioxidants (e.g., BHA and BHT, for example) with these natural long-chain oils (e.g., from at least about 8 carbon atoms to 30 or more carbon atoms in the primary aliphatic chain), and their ethyl esters, fats or fatty materials tends to slightly improve their oxidative stability, but do not provide dramatic improvements in levels of OSI in these oils. However, there is always a demand for compositions that exhibit longer and longer oxidative stability. Therefore, there is therefore a clear need for the ability to provide an oxidatively ultra-composition for uses in emollients and the like.

Pure moringa oil has an oxidative stability of 29.6 hours. According to data on other natural oils, the addition of a small amount of a tocopherol should increase the oxidative stability of the oil by about 150%. Thus, one of ordinary skill in the arts would expect that the addition of a small amount of tocopherols to moringa oil would increase its oxidative stability from 29.6 to around 44.4 hours. While this slight theoretical increase may be beneficial, it has been unexpectedly determined that the actual increase in oxidative stability is 133.3 hours, or an increase of 450%. This dramatic increase is extremely useful for compositions such as emollients since it extends the emollient shelf live significantly beyond that of any other natural, or naturally derived, emollient composition. Moreover, it has been surprisingly determined that further addition of a supplemental additive extends the oxidative stability even more.

Heretofore, it has been impossible to use substantial quantities of ethyl esters in cosmetic formulations despite their beneficial "dry emollient" properties. Now that a composition has been produced that is an ultra-stable emollient, especially the ethyl ester, meaningful quantities of this material can be used and at the same time, the formulation will remain oxidatively stable. Thus, the present invention provides emollient compositions displaying drastically improved oxidation resistance comprising moringa oil (or derivatives thereof), fats, or fatty material, and at least one tocopherol. The tocopherols may be used in amounts from about 0.02% by weight of the composition to about 5% by weight of the composition, depending upon the particular formulation, and other additives in the composition. In general, relatively low amounts of the tocopherols are highly effective.

EXAMPLES

The following non-limiting examples are provided for further enablement of the practice of the invention and are not to be construed as specifically limiting the practice of the invention in any way.

Table 2 discloses representative percent compositions of fatty acid moieties contained within the moringa oil used in the formulations presented herein.

TABLE 2

| Fatty Acid | | Composition % | | |
| --- | --- | --- | --- | --- |
| | | Composition 1 (Raw) | Composition 2 (Raw) | Composition 2 (Refined) |
| Myristic | C14:0 | 0.1 | 0.1 | 0.1 |
| Palmitic | C16:0 | 6.0 | 6.9 | 7.0 |
| Palmitoleic | C16:1 | 1.8 | 2.1 | 2.5 |
| Stearic | C18:0 | 5.4 | 5.0 | 5.0 |
| Oleic | C18:1 | 72.1 | 78.3 | 78.4 |
| Linoleic | C18:2 | 0.7 | 0.7 | 0.8 |
| Linolenic | C18:3 | 0.2 | 0.1 | 0.1 |
| Arachidic | C20:0 | 3.4 | 2.1 | 1.9 |
| Eicosenoic | C20:1 | 2.1 | 1.6 | 1.5 |
| Behenic | C22:0 | 6.7 | 2.6 | 2.2 |
| Lignoceric | C24:0 | 1.1 | 0.2 | 0.1 |

Table 3 reports the OSI values of a variety of different natural oils (both with and without tocopherols) thereby illustrating the ultrastabilization that the addition of tocopherols to moringa oil provides. Further reported in Table 3 are the percent increase in stability provided by the addition of tocopherols, percent polyunsaturation of the different oils, and the iodine values of the different oils.

TABLE 3

Action of Tocopherols on Refined Seed Oils

| Oil | OSI (Pure) | OSI (w/tocopherol) | % Increase | % poly-unsaturates | Iodine Value |
|---|---|---|---|---|---|
| Traditional Sunflower | 2.7 | 4.1 | 151.9 | 69.3 | 136.3 |
| Almond | 5.2 | 9.8 | 187.5 | 24.6 | 99.8 |
| Sesame | 8.6 | 9.5 | 110.5 | 43.9 | 110.4 |
| Apricot | 10.7 | 12.9 | 120.6 | 28.7 | 103.8 |
| High-Oleic Safflower | 11.8 | 17.9 | 151.7 | 13.7 | 91.0 |
| Coriander | 13.4 | 18.5 | 138.0 | 16.6 | 96.8 |
| Avocado | 14.0 | 21.0 | 150.0 | 15.4 | 86.2 |
| Crambe | 14.8 | 16.5 | 111.5 | 15.9 | 91.3 |
| Palm | 21.3 | 30.6 | 143.7 | 8.0 | 47.3 |
| High-Oleic Sunflower | 22.4 | 63.3 | 282.6 | 4.9 | 84.8 |
| Macadamia | 26.5 | 103.0 | 388.7 | 3.4 | 76.0 |
| Moringa | 29.6 | 133.3 | 450.3 | 0.7 | 65.5 |

Table 4 reports the OSI values of a variety of different oil ethyl esters (both with and without tocopherols) thereby illustrating the ultrastabilization provided by the addition of tocopherols to derivatives, such as moringa oil ethyl ester. Further reported in Table 4 are the percent change in stability provided by the addition of tocopherols in combination with at least one supplemental additive such as the free-radical scavengers malic acid, kojic acid, and ascorbic acid, and percent polyunsaturation of the different ethyl esters. Examination of Table 4 reveals that the addition of tocopherols to the ethyl ester of moringa oil increases the stability from 1.3 hours to 9.8 hours (754%). Unexpectedly, the addition of the other malic acid, kojic acid, and ascorbic acid alone either reduced the stability or left it virtually unaffected. Even more unexpectedly, addition of tocopherols combined with the other supplemental additives vastly increased the stability of moringa oil ethyl ester: from 1.3 to 162.5 hrs (12,500%) (tocopherols and malic acid); from 1.3 to 376 hrs (28,923%)(tocopherols and kojic acid); and from 1.3 to 121.0 hrs (9,308%) (tocopherols and ascorbic acid). This ultrastabilization is surprisingly greater (orders of magnitude) than that found for the ethyl esters of other naturally occurring oils.

Further, it is expected that including into the composition of the present invention formulations that in themselves contain anti-oxidants, especially tocopherols, will further enhance the ultra-stability of the composition of the present invention. While there is a preferred range for the amount of tocopherols added to the present invention as disclosed herein, additional antioxidants have been shown to further increase the stability (meaning that the stabilization effect provided by the tocopherols has not leveled off).

As can be seen from the above, the addition of tocopherols, and especially tocopherols combined with other supplemental additives such as malic acid, kojic acid, and ascorbic acid, to moringa oil and moringa oil ethyl ester produces super-stable compositions, as evidenced from the OSI results. The data clearly shows that this addition provides a surprising and unexpected stabilization of the moringa oil and ethyl ester thereof.

Slip properties (lubricity) of the compositions of the present invention were measured using a modified Cadicamo method, discussed in more detail in Soap &Cosmetics, June 2001, which is herein incorporated in its entirety into the instant application. These measurements revealed that the compositions of the present invention demonstrate a slip angle that is lower (greater slipperiness) than that of castor oil, one of the most slippery natural products known (7.0° as compared to 7.4°). This unexpectedly low value of slip (higher lubricity or slipperiness) is an extremely useful property in many products, especially cosmetic and other skin related applications. Further, when combining moringa oil, and its esters, into cosmetic formulations, it has been found that the break strength of the various formulas is greatly increased.

The slip testing was done using the Floratech method of placing an oil covered disk on a glass plate. An edge of the glass plate is inclined until the oil covered disk begins to slip (first slip). The incline value, measured in degrees, is reported as the slip value. The moringa oil sample was slip tested thirteen times with the following results.

(1) 7.5 (2) 6.5 (3) 7.0 (4) 9.0 (5) 9.0 (6) 9.0 (7) 12 (8) 12 (9) 8 (10) 4 (11) 4 (12) 4 (13) 5: Ave=7.5

This average value indicates the highest slip of any known oil produced from a natural product.

The spread testing was done using the Floratech method of adding 20 drops the material to be tested on P5 filter paper. The percentage of the whole paper that was covered by the oil in question is measured after 10 minutes and recorded as the percent spread value. A moringa oil sample was tested for spread five times with the following results.

(1) 15.47% (2) 16.10% (3) 14.90% (4) 15.64% (5) 15.43%: Ave=15.5%

This average value is a medium value, typical for many oils produced from natural products.

The emollient compositions of the present invention are found to be most useful in cosmetic applications including, but not limited to: creams, lotions, and liquid foundation (slip); massage oils and the like (slip, oxidative stability); pressed products such as eye shadow, blush, and powder (slip); molded products such as lipstick, lip balm, foundation, blush, eye liner, eye shadow, mascara and the like (slip, break strength); hair care products, such as leave in conditioners, relaxers, hair dyes and other applications where there is stress on the oxidative stability of the composition. Example formulations of various products, exhibiting the usefulness of the decreased slip and/or increase break strength are illustrated below.

Massage Oil:

It is noted from above that moringa oil, while having a medium spread value, is very slippery (more slippery that castor oil, the most slippery natural product oil). This makes moringa oil, and its various esters, an excellent component used in massage oil formulations. At least three different formulations, described below, were made for efficacy comparison. Each formula was applied to the skin of several volunteers and the results were noted.

Formula 1 had a "dry" feel, with a slight "drag" as it is moved across the skin. It has a "light" feel, not heavy and oily, and it leaves a somewhat dry look on the skin. It may work well as a massage oil when some skin friction is required.

Formula 2 has a heavier, oily feel, with a good degree of slip. It glistens on the skin, and has a little bit of a wet look. This version is suitable as an "oily" massage oil.

Formula 3 is the moringa oil formulation. It has excellent spread and slip qualities. It has a dry feel with increase slip over the first two formulations. It is an excellent massage oil.

Using the unique properties of Moringa Oil, this formula provides a smooth, high slip feel desirable in a massage oil. Floraesters provides an emollient skin feel, while Floramac 10 provides a high degree of spread over the surface.

| Trade Name | INCI Name | Supplier | % wt./wt. |
|---|---|---|---|
| Formula 1 | | | |
| Floramac 10 | Ethyl Macadamiate | Floratech | 49.0 |
| Floraesters 15 | Jojoba Esters | Floratech | 15.0 |
| Florasun 90 | Helianthus Annuus (Sunflower) Oil | Floratech | 15.0 |
| Macadamia Nut Oil | Macadamia Nut Oil | Floratech | 20.0 |
| Tocopheryl Acetate CG | Tocopheryl Acetate | Roche | 1.0 |
| Total | | | 100.0 |
| Formula 2 | | | |
| Floramac 10 | Ethyl Macadamiate | Floratech | 25.0 |
| Floraesters 15 | Jojoba Esters | Floratech | 15.0 |
| Florasun 90 | Helianthus Annuus (Sunflower) Oil | Floratech | 15.0 |
| Macadamia Nut Oil | Macadamia Nut Oil | Floratech | 15.0 |
| Canola Oil | Canola Oil | Floratch | 29.0 |
| Tocopheryl Acetate CG | Tocopheryl Acetate | Roche | 1.0 |
| Total | | | 100.0 |
| Formula 3 | | | |
| Floramac 10 | Ethyl Macadamiate | Floratech | 49.0 |
| Floraesters 15 | Jojoba Esters | Floratech | 15.0 |
| Florasun 90 | Helianthus Annuus (Sunflower) Oil | Floratech | 15.0 |
| Moringa Oil | Moringa Oleifera Seed Oil | Floratech | 20.0 |
| Tocopheryl Acetate CG | Tocopheryl Acetate | Roche | 1.0 |
| Total | | | 100.0 |

Mixing Procedure: Combine all ingredients at room temperature with rapid propeller agitation.

Moringa Oil Lipstick:

Lipsticks made using moringa oil in the formulation showed a surprising increase in the break strength. Using the Chatillon DFM-10 Break Strength meter, it was determined that lipstick produced using moringa oil (formula 4) broke under an average force of 0.668 kg. A standard lipstick formula (formula 5) demonstrated a breakstrength of 0.527 kg breaking force. The only difference between the standard formulation and the moringa oil formulation is the substitution of 15% moringa oil for 15% isopropyl jojobate in the standard formulation. All other ingredients in the formula are exactly the same.

The standard HLB test was performed on Moringa Oil and it was determined that the required HLB is 6.4

Five volunteers were given lipsticks to test with the following results. The two lipsticks were the standard formulation and the moringa oil formulation.

Ease of Application

With regard to application, the moringa oil formulation scored higher than the standard formulation. On a scale of 1 to 10, with 10 being the best, the moringa oil formulation scored 6.00 and the standard formulation scored 5.75. Comments on the standard formulation include "does not glide very well", "very hard stick", and "a little drag at first". Comments on the moringa oil formulation include "also a very hard stick", and "also a little drag".

Permanence

With regard to permanence, the standard formulation scored slightly better than the moringa oil formulation. On a scale of 1 to 10, with 10 being the best, the standard formulation scored 6.25 and the moringa oil formulation scored 6.00.

Color Transferability

With regard to color transferability, the standard formulation scored slightly better than the moringa oil formulation. On a scale of 1 to 10, with 10 being the best, the standard formulation scored 8.00 and the moringa oil formulation scored 7.50.

Feathering

With respect to feathering, one person stated that the standard formulation "feathered" past the lips. No subject stated that the moringa oil formulation "feathered" past the lips. This was a "yes", "no" question.

Color Finish: Matte=1 to Glossy=10

With respect to color finish, the moringa oil formulation showed a slightly more matte finish with a score of 4.25 as compared to the standard formulation, which scored 4.75. One comment on the moringa oil formulation was "I like this look! It doesn't feel dry on lips".

Glide or Slip

With respect to glide or slip, the moringa oil formulation scored slightly higher than the standard formulation. On a scale of 1 to 10, with 10 being the best, the moringa oil formulation scored 5.75 and the standard formulation scored 5.25.

Taste

With respect to taste, most subjects reported "no" for both formulations with only one person for each formulation claiming a slight taste problem.

A lipstick was formulated using replacing 1.0% hydrogenated moringa oil (formula 6) for 1.0% hydrogenated jojoba oil (FE-70) in the standard formulation. The break strength for this formulation was 0.512 kg, which is almost identical to the standard formulation break strength. It should be noted that the hydrogenated moringa oil formulation had a more matte finish when removed from the mold when compared to the standard formulation and the higher percentage moringa oil formulation.

The substitution of moringa oil for the traditional binding/slip oil provides a formulation with improved wetting and dispersal properties. This yields a lipstick with a smoother, more even coverage. It has been found that the moringa oil provides the high slip and gloss to the stick as well as the enhanced break strength. This shade does not exhibit syneresis.

| Phase | Trade Name | INCI Name | Supplier | % wt./wt. |
|---|---|---|---|---|
| | | Formula 4 | | |
| A. | Crystal O | Ricinus Communis (Castor) Seed Oil | CasChem | Q.S. |
| | IPJ | Isopropyl Jojobate | Floratech | 15.0 |
| | Floraesters 70 | Jojoba Esters | Floratech | 1.0 |
| | Carnauba Wax #1 Yellow SP 63 | Copernicia Cerifera (Carnauba) Wax | Strahl & Pitsch | 4.0 |
| | Candelilla Wax SP 75 | Euphorbia Cerifera (Candelilla) Wax | Strahl & Pitsch | 5.0 |
| | Yellow Beeswax SP 6P | Beeswax | Strahl & Pitsch | 3.5 |
| | Microcrystalline Wax SP 18 | Microcrystalline Wax | Strahl & Pitsch | 4.0 |
| | Preservative | — | | Q.S. |
| | CAB-O-SIL M-5 | Silica | Cabot | 0.2 |
| B. | Crystal O | Ricinus Communis (Castor) Seed Oil | CasChem | 13.0 |
| | Arlacel P-100 | Polyhydroxystearic Acid | Uniqema | 0.5 |
| | Titanium Dioxide 10-34-PC-0748 | Titanium Dioxide | Noveon | 5.5 |
| | Pur Oxy Red B.C. 34-3511 | Iron Oxides | Noveon | 4.0 |
| | D&C Red 30 Talc Lake 10-31-DA-3130 | D&C Red No 30 Talc Lake | Noveon | 2.5 |
| | FD&C Blue No. 1 Aluminum Lake | FD&C Blue No. 1 Aluminum Lake | Warner-Jenkinson | 0.1 |
| | Pur Oxy Black B.C. 34-3068 | Iron Oxides | Noveon | 0.5 |
| C. | Covi-Ox T-70 | Tocopherols | Cognis | 0.1 |
| | TOTAL: | | | 100.0 |
| | | Formula 5 | | |
| A. | Crystal O | Ricinus Communis (Castor) Seed Oil | CasChem | Q.S. |
| | Moringa Oil | Moringa Oleifera Seed Oil | Floratech | 15.0 |
| | Floraesters 70 | Jojoba Esters | Floratech | 1.0 |
| | Carnauba Wax #1 Yellow SP 63 | Copernicia Cerifera (Carnauba) Wax | Strahl & Pitsch | 4.0 |
| | Candelilla Wax SP 75 | Euphorbia Cerifera (Candelilla) Wax | Strahl & Pitsch | 5.0 |
| | Yellow Beeswax SP 6P | Beeswax | Strahl & Pitsch | 3.5 |
| | Microcrystalline Wax SP 18 | Microcrystalline Wax | Strahl & Pitsch | 4.0 |
| | Preservative | — | | Q.S. |
| | CAB-O-SIL M-5 | Silica | Cabot | 0.2 |
| B. | Crystal O | Ricinus Communis (Castor) Seed Oil | CasChem | 13.0 |
| | Arlacel P-100 | Polyhydroxystearic Acid | Uniqema | 0.5 |
| | Titanium Dioxide 10-34-PC-0748 | Titanium Dioxide | Noveon | 5.5 |
| | Pur Oxy Red B.C. 34-3511 | Iron Oxides | Noveon | 4.0 |
| | D&C Red 30 Talc Lake 10-31-DA-3130 | D&C Red No 30 Talc Lake | Noveon | 2.5 |
| | FD&C Blue No. 1 Aluminum Lake | FD&C Blue No. 1 Aluminum Lake | Warner-Jenkinson | 0.1 |
| | Pur Oxy Black B.C. 34-3068 | Iron Oxides | Noveon | 0.5 |
| C. | Covi-Ox T-70 | Tocopherols | Cognis | 0.1 |
| | TOTAL: | | | 100.0 |
| | | Formula 6 | | |
| A. | Crystal O | Ricinus Communis (Castor) Seed Oil | CasChem | Q.S. |
| | Hydrogenated Moringa oil | Hydrogenated Moringa Oleifera Seed Oil | Floratech | 1.0 |
| | Floraesters IPJ | Isopropyl Jojobate (and) Jojoba Alcohol (and) Jojoba Esters | Floratech | 15.0 |
| | Carnauba Wax #1 Yellow SP 63 | Copernicia Cerifera (Carnauba) Wax | Strahl & Pitsch | 4.0 |
| | Candelilla Wax SP | Euphorbia Cerifera (Candelilla) | Strahl & Pitsch | 5.0 |

-continued

| Phase | Trade Name | INCI Name | Supplier | % wt./wt. |
|---|---|---|---|---|
|  | 75 Yellow Beeswax SP 6P | Wax Beeswax | Strahl & Pitsch | 3.5 |
|  | Microcrystalline Wax SP 18 | Microcrystalline Wax | Strahl & Pitsch | 4.0 |
|  | Preservative | — |  | Q.S. |
|  | CAB-O-SIL M-5 | Silica | Cabot | 0.2 |
| B. | Crystal O | Ricinus Communis (Castor) Seed Oil | CasChem | 13.0 |
|  | Arlacel P-100 | Polyhydroxystearic Acid | Uniqema | 0.5 |
|  | Titanium Dioxide 10-34-PC-0748 | Titanium Dioxide | Noveon | 5.5 |
|  | Pur Oxy Red B.C. 34-3511 | Iron Oxides | Noveon | 4.0 |
|  | D&C Red 30 Talc Lake 10-31-DA-3130 | D&C Red No 30 Talc Lake | Noveon | 2.5 |
|  | FD&C Blue No. 1 Aluminum Lake | FD&C Blue No. 1 Aluminum Lake | Warner-Jenkinson | 0.1 |
|  | Pur Oxy Black B.C. 34-3068 | Iron Oxides | Noveon | 0.5 |
| C. | Covi-Ox T-70 | Tocopherols | Cognis | 0.1 |
|  |  | TOTAL: |  | 100.0 |

Mixing Procedure: Combine ingredients of Phase A and heat to 85° C. with moderate agitation. Combine Phase B and pass two times through a 3-roll mill. Add Phase B to Phase A with propeller agitation. Cool batch to 75° C., add Phase C and mix with propeller agitation. Fill mold as soon as possible.

Tinted Moisturizer

This formula helps soothe, moisturize, and protect the skin. Moringa Oil provides a high degree of slip to the formula, facilitating application. Floramac 10 allows the formula to spread easily and evenly. With UV protection, this formula provides the skin with a healthy, radiant glow.

| Phase | Trade Name | INCI Name | Supplier | % wt./wt. |
|---|---|---|---|---|
|  |  | Formula 7 |  |  |
| A | Water | Water | — | Q.S. |
|  | Carbopol 940 | Carbomer | Noveon | 0.3 |
|  | Glycerin | Glycerin | Transmacro Inc | 5.0 |
|  | Butylene Glycol | Butylene Glycol | Celanese | 5.0 |
|  | Preservative | — |  | Q.S. |
| B | Floramac 10 | Ethyl Macadamiate | Floratech | 2.0 |
|  | Softisan 142 | Hydrogenated Coco-Glycerides | Condea | 2.0 |
|  | Mineral Oil | Mineral Oil | Penreco | 4.0 |
|  | Pristerene 4911 | Stearic Acid | Uniqema | 4.0 |
|  | White Petrolatum | Petrolatum | Penreco | 3.0 |
|  | Lanette 18 | Stearyl Alcohol | Cognis | 3.0 |
|  | Moringa Oil | Moringa Oleifera Seed Oil | Floratech | 4.0 |
|  | Lanette 16 NF | Cetyl Alcohol | Cognis | 3.0 |
|  | Lexemul 515 | Glyceryl Stearate | Inolex | 2.0 |
|  | Parsol MCX | Ethylhexyl Methoxycinnamate | Roche | 4.00 |
|  | Eusolex T-45D | Isononyl Isononoate (and) Titanium Dioxide (and) Alumina (and) Simethicone (and) Polyglyceryl-6 Ricinoleate | Rona | 15.00 |
| C | Pur Oxy Red 34-3080 | Iron Oxide | Noveon | 0.30 |
|  | Pur Oxy Yellow 34-3170 | Iron Oxide | Noveon | 1.65 |
|  | Pur Oxy Red 34-3551 | Iron Oxide | Hilton Davis | 0.36 |
|  | Pur Oxy Black 34-3068 | Iron Oxide | Noveon | 0.42 |
|  | Talc Supra H | Talc | Luzenac | 4.50 |
| D | 50% Sodium Hydroxide Soln. | Sodium Hydroxide | Fisher | 0.5 |
|  |  | Total= |  | 100.0 |

Mixing Procedure: Heat the water of Phase A to 75F. With medium propeller agitation, sift in the Carbopol 940. Allow time for complete hydration of the Carbomer. Premix the preservatives in the butylene glycol. Add the glycerin and then the premixed butylene glycol fraction to the water phase. Add all of the components of Phase B together. Heat the components to 75F with propeller agitation until complete mixing has been achieved. Weigh all the components of Phase C together. Using a homomixer, add Phase B to Phase A with high rpm homomixer agitation. With continued homomixer agitation sift in the pigments of Phase C. With continued homomixer agitation, add Phase D to Phase ABC. Pour mix while still hot into tubes or containers.

In addition to the essential ingredients in the emollient compositions of the present invention, further material may be present in the composition for functional or aesthetic reason. Additional antioxidants from the classes described herein and/or antioxidants, including tocotrienols (compounds homologous to tocopherols that differ by the presence of three unsaturated bonds in the phytyl side chain), and oryzanol (a mixture of ferulic acid esters of sterols, e.g., beta-sitosteryl ferulate and methyl ferulate, and triterpene alcohols, e.g., 24-methylenecycloartenyl ferulate; see Bailey's Industrial Oil and Fat Products, 4th Ed., John Wiley, New York, 1979, volume 1, pages 407 to 409) may be present. Fragrances, colorants (e.g., dyes or pigments), topically applied medications, UV absorbers, whitening agents, emulsifying agents, binders, scrubbing particulates, and the like may be present.

Fatty elements in addition to the stabilized moringa oil, hydrogenated moringa oil, and alkyl ester thereof that may be used can be selected from mineral oils like paraffin or petroleum oils, silicon oils, vegetable oils like coconut, almond, apricot, corn, jojoba, olive, avocado, sesame, palm, eucalyptus, rosemary, lavender, pine, thyme, mint, cardamon, orange blossoms, soy beans, bran, rice, colza, and castor oils, animal oils and fats like tallow, lanolin, butter oil, fatty acid esters, fatty alcohol esters, waxes whose melting point is the same as the skin's (animal waxes like bee's wax, carnauba or candelilla waxes, mineral waxes like microcrystalline waxes and synthetic waxes like polyethylene or silicone waxes). All acceptable oils used in cosmetology can be used, like the ones that have been mentioned in the CTFA's book, Cosmetic Ingredient Handbook, First edition, 1988, The Cosmetic, Toiletry and Fragrance Association, Inc., Washington (hereinafter, "CTFA").

Cosmetically or dermatologically active substances may be added to the composition of the present invention, meaning active cosmetics chosen from anti-acne agents, anti-microbial agents, anti-perspiration agents, astringents, deodorants, hair removers, external analgesics, agents for hair conditioning, skin conditioning, sun protection, vitamins, catechines, flavonoids, ceramides, fatty substances, polyunsaturated fatty acids, essential fatty acids, keratolytic agents, enzymes, anti-enzymes, moisteners, anti-inflammatory substances, detergents, perfumes, and mineral substances for synthetic coverings. These substances may represent from 1 to 20% by weight of the total weight of the composition.

Detergent or foaming agents, for example, may include disodic cocoamphodiacetate salts; lauroylether sulfosuccinate disodic salts; the vegetable protein acylates; the cocoyl gutamate triethanolamine salts; the lauroyl sarcosinate sodium salts; the glucoside decyl-ethers; and the sodium sulfate lauroyl ethers.

Pasty active compounds like lanolin by-products (acetyl lanolin, lanolin, and lanolin alcohols; cholesterol by-products, like cholesterol esters (12 cholesteryl hydroxy stearate); pantaetythritol hydroxylated esters, linear monoesters like butyl stearate, arachidyl propionate or stearyl heptanoate, and triglycerides with a fatty chain less that C16 can also be used. These substances may be water-soluble, lipid-soluble, or lipid-soluble and water soluble at the same time, or dispersible. They can be chosen from the compounds that are in CTFA at pages 51 to 101.

Surface active agents, cationic, anionic, non-ionic and/or Zwitterionic may be used. These surface agents can be chosen, for example, from the hydrophilic surface agents, like glycols, such as hexylene glycol, butylene-1,2 glycol, ethyl-2-hexyl sulfosuccinate; oxyethylene octylphenol (9, and the salts derived from cocoyl and lauroyl collagen, sorbitan palmitate, and the polyoxyethylene byproducts of sorbitol palmitate esters, salts of fatty chain quaternary ammonium. Suitable anionic surfactants which may be used include the water-soluble alkali metal or ammonium salts having alkyl radicals containing from abut 8 to about 22 carbon atoms, the term alkyl being used to include the alkyl portion of higher acyl radicals. Examples of suitable synthetic anionic surfactants are sodium or ammonium alkyl sulfates, especially those obtained by sulfating higher ($C_8$–$C_{18}$) alcohols produced, for example, from tallow or coconut oil; alkyl ($C_9$–$C_{20}$) benzene sulfonates, particularly sodium linear secondary alkyl ($C_{10}$–$C_{15}$) benzene sulfonates; alkyl glyceryl ether sulfates, especially those ethers of the higher alcohols derived from tallow or coconut oil and synthetic alcohols derived from petroleum; coconut oil fatty monogyceride sulfates and sulfonates; salts of sulfuric acid esters of higher ($C_8$–$C_{18}$) fatty alcohol-alkylene oxide, particularly ethylene oxide reaction products; the reaction products of fatty acids such as coconut fatty acids esterified with isoethionic acid and neutralized with sodium hydroxide; sodium and potassium salts of fatty acid amides of methyl taurine; alkane monosulfonates such as those derived from reacting alpha-olefins ($C_8$–$C_{20}$) with sodium bisulfite and those derived from reacting paraffins with $SO_2$ and $C_{12}$ and then hydrolyzing with a base to produce a random sulfonate; and olefin sulfonates which term is used to describe the material made by reacting olefins, particularly $C_{10}$–$C_{20}$ alpha-olefins, with $SO_3$ and then neutralizing and hydrolyzing the reaction product. The preferred anionic surfactants are sodium or ammonium ($C_{10}$–$C_{18}$) alkyl sulfates and ($C_{10}$–$C_{18}$) alkyl polyethoxy (1–11 EO, ethylene oxide) sulfates and mixtures thereof having differing water solubilities.

Particularly preferred anionic surfactants comprise a mixture of a $C_{10}$–$C_{18}$ alkyl sodium or ammonium sulfate or sulfonate or a $C_{14}$–$C_{18}$ alpha-olefin sodium or ammonium sulfonate (AOS) and a $C_8$–$C_{12}$ alkyl polyethyoxy (2–4 EO) sodium or ammonium sulfate. Mixtures containing a major amount of the alkyl sulfates, olefin sulfonates or alkyl alkoxy sulfates with aryl sulfonates such as sodium cumene sulfonate, sodium xylene sulfonate and sodium benzene sulfonate are also optional.

The amount of anionic surfactant present in the composition, which is moringa oil (or its derivatives) combined with tocopherols, will generally range from about 0 or 1% or 4 to 12% by weight (total ingredients) by weight. The amphoteric or Zwitterionic surfactant, may optionally be present at a level of at least abut 0.1 or at least about 0.25 percent by weight of the total composition, per 1 part by weight of the content of anionic surfactant present in the composition.

Examples of amphoteric surfactants that may be used in the composition of the invention are betaines and compounds that can be broadly described as derivatives of aliphatic secondary and tertiary amines in which the aliphatic radical can be straight chain or branched and wherein one of the aliphatic substituent contains from abut 8 to 18 carbon atoms and one contains an ionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as prepared by reacting dodecylamine with sodium isethionate, N-higher alkyl aspartic acids and the products sold under the trade name "Miranol".

Makeup or cosmetic compositions comprising the present invention may also contain as an optional ingredient, a film forming skin tightening agent, particularly a plant derived biological polysaccharide cosmetic ingredient that may be combined with a casein hydrolysate.

The polysaccharides that can be used in the practice of the invention include, for example, lecithin, pectin, karaya gum, locust bean gum, xanthan gum and mixtures thereof. The polysaccharides are preferably used in the present compositions in combination with a casein hydrolysate.

Suitable co-emulsifiers are both known w/o (water in oil) and o/w (oil in water) emulsifiers. Typical examples of fats are glycerides while suitable waxes include inter alia beeswax, paraffin wax or microwaxes. Suitable thickeners are, for example, crosslinked polyacrylic acids and derivatives thereof, polysaccharides, more particularly xanthan gum, guar guar, agar agar, alginates and tyloses, carboxymethyl cellulose and hydroxyethyl cellulose, also fatty alcohols, monoglycrides and fatty acids, polyacrylates, polyvinyl alcohol and polyvinyl pyrrolidone. In the context of the invention, biogenic agents are, for example, plant extracts, protein hydrolyzates and vitamin complexes. Typical film formers are, for example, polyvinyl pyrolidone, vinyl pyrolidone/vinyl acetate copolymers, polymers of the acrylic acid series, quaternary cellulose derivatives and similar compounds. Suitable preservatives are, for example formaldehyde solution, p-hydroxybenzoate or sorbic acid. Suitable pearl esters are, for example, glycol distearic acid esters, such as ethylene glycol distearate, and also fatty acids and fatty acid monoglycol esters. The dyes used may be selected from many of the substances that are permitted and suitable for cosmetic purposes, as listed for example in the publication "Kosmetische Farbemittel" of the Farbstoffkommission der Deutschen pages 81–106. These dyes are typically used in concentrations of 0.001 to 0.1% by weight, based on the mixture as a whole.

The total percentage content of auxiliaries and additives may be 1 to 50% by weight and may be 5 to 40% by weight, based on the formulation. The formulations may be produced in known manner, i.e. for example by hot, cold, ho-hot/cold or PIT emulsification. These are purely mechanical processes that do not involve a chemical reaction. The cosmetic and/or pharmaceutical formulations may have a water content of 25 to 95% by weight and preferably 50 to 75% by weight.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

TABLE 4

| ETHYL ESTER OF | NO ADDITIVE | TOCOPH- EROLS | KOJIC ACID | MALIC | ASCORBIC | TOCOPH- EROLS + MALIC ACID | TOCOPH- EROLS + KOJIC ACID | TOCOPH- EROLS + ASC. ACID | % METHYLENE UNSATURATION |
|---|---|---|---|---|---|---|---|---|---|
| MORINGA | 1.3 | 9.8 | 0.6 | 1.7 | 0.7 | 162.5 | 376 | 121.0 | 0.7 |
| MEADOWFOAM | 48.0 | 103.2 | 83.0 | 110.2 | 183.1 | 169.1 | 125.1 | 265.7 | 1 |
| BABASSU | 5.8 | 23.3 | 7.9 | 41.0 | 176.5 | 122.6 | 138.1 | 162.8 | 2 |
| MACADAMIA | 4.5 | 49.5 | 7.5 | 5.6 | 17.6 | 88.8 | 86.0 | 234.4 | 3 |
| HYBRID SUNFLOWER | 2.2 | 10.0 | 13.1 | 21.7 | 65.6 | 73.4 | 76.3 | 139.7 | 4 |
| HIGH-OLEIC SAFFLOWER | 2.7 | 8.9 | 10.7 | 13.0 | 48.3 | 31.3 | 29.8 | 81.3 | 12 |
| MINK | 3.0 | 6.6 | 7.6 | 9.4 | 18.8 | 21.3 | 21.1 | 117.4 | 15 |
| SWEET ALMOND | 1.7 | 5.2 | 3.4 | 5.7 | 21.3 | 13.5 | 11.3 | 39.8 | 25 |
| CANOLA | 3.4 | 6.4 | 6.3 | 6.2 | 38.0 | 10.5 | 8.3 | 42.3 | 28 |
| SESAME | 4.7 | 6.0 | 8.3 | 9.7 | 37.5 | 12.9 | 8.1 | 44.6 | 44 |
| MILKWEED | 1.3 | 1.8 | 2.0 | 2.4 | 14.7 | 6.9 | 4.6 | 7.4 | 51 |

What is claimed is:

1. A cosmetic composition, selected from the group consisting of creams, lotions, sunscreens, perfume sticks, massage oils, eye shadows, blushes, powders, lipsticks, lip balms, foundations, eye liners, mascaras, leave in conditioners, relaxers, and hair dyes having high slit characteristic comprising a long-chain oil of moringa and at least one tocopherol, said long-chain oil has a methylene interrupted unsaturation of less than 1%. where the long-chain oil of moringa has a slip value greater than that of castor oil, 7.0 as measured by a modified Cadicamo method and further comprising at least one supplemental additive, wherein the at least one supplemental additive selected from the group consisting of kojic acid, malic acid, and ascorbic acid, wherein said tocopherol is present in an amount of from 0.01 to 5% by weight of said long-chain oil, wherein said tocopherol and said at least one supplemental additive in combination provide a greater oxidation stability to the lone-chain oil relative to the oxidation stability of the oil alone.

2. The composition according to claim 1, wherein the long-chain oil is a derivative of the oil produced from *Moringa oleifera*.

3. An improved binder for cosmetic formulation comprising a long-chain oil of moringa, said long-chain oil has a methylene interrupted unsaturation of less than 1%, where if said binder is included into a cosmetic formulation then a greater break strength relative to a standard formulation is provided.

4. The composition according to claim 3, wherein the long-chain oil is a derivative of the oil produced from *Moringa oleifera*.

5. The composition according to claim 3, where the long-chain oil of moringa has a slip value greater than that of castor oil, 7.0 as measured by a modified Cadicamo method.

6. The composition according to claim 3, further comprising at least one tocopherol, wherein said tocopherol provides a greater oxidation stability to the long-chain oil relative to the oxidation stability of the oil alone.

7. The composition according to claim 6 further comprising at least one supplemental additive, wherein the at least one supplemental additive selected from the group consisting of kojic acid, malic acid, and ascorbic acid, wherein said tocopherol is present in an amount of from 0.01 to 5% by weight of said long-chain oil, wherein said tocopherol and said at least one supplemental additive in combination provide a greater oxidation stability to the long-chain oil relative to the oxidation stability of the oil alone.

8. The composition according to claim 4, further comprising at least one tocopherol, wherein said tocopherol provides a greater oxidation stability to the long-chain oil relative to the oxidation stability of the oil alone.

9. The composition according to claim 8 further comprising at least one supplemental additive, wherein the at least one supplemental additive selected from the group consisting of kojic acid, malic acid, and ascorbic acid, wherein said tocopherol is present in an amount of from 0.01 to 5% by weight of said long-chain oil, wherein said tocopherol and said at least one supplemental additive in combination provide a greater oxidation stability to the long-chain oil relative to the oxidation stability of the oil alone.

10. The composition according to claim 5, further comprising at least one tocopherol, wherein said tocopherol provides a greater oxidation stability to the long-chain oil relative to the oxidation stability of the oil alone.

11. The composition according to claim 9 further comprising at least one supplemental additive, wherein the at least one supplemental additive selected from the group consisting of kojic acid, malic acid, and ascorbic acid, wherein said tocopherol is present in an amount of from 0.01 to 5% by weight of said long-chain oil, wherein said tocopherol and said at least one supplemental additive in combination provide a greater oxidation stability to the long-chain oil relative to the oxidation stability of the oil alone.

12. The emollient composition of claim 3 wherein said composition is used in cosmetic applications selected from the group consisting of creams, lotions, and liquid foundations; massage oils; pressed products, such as eye shadow, blush, and powder; molded products, such as lipstick, lip balm, foundation, blush, eye liner, eye shadow, mascara; and hair care products, such as leave in conditioners, relaxers, hair dyes.

13. A composition for solid phase cosmetic formulations comprising a long-chain oil of moringa, said long-chain oil has a methylene interrupted unsaturation of less than 1%, where the long-chain oil of moringa has a slip value greater than that of castor oil, 7.0 as measured by a modified Cadicamo method, and if included into a cosmetic formulation, provides a greater break strength relative to a standard formulation.

14. The composition according to claim 13, wherein the long-chain oil is a derivative of the oil produced from *Moringa oleifera*.

15. The composition according to claim 13, further comprising at least one tocopherol, wherein said tocopherol provides a greater oxidation stability to the long-chain oil relative to the oxidation stability of the oil alone.

16. The composition according to claim 15 further comprising at least one supplemental additive, wherein the at least one supplemental additive selected from the group consisting of kojic acid, malic acid, and ascorbic acid, wherein said tocopherol is present in an amount of from 0.01 to 5% by weight of said long-chain oil, wherein said tocopherol and said at least one supplemental additive in combination provide a greater oxidation stability to the long-chain oil relative to the oxidation stability of the oil alone.

17. The composition according to claim 14, further comprising at least one tocopherol, wherein said tocopherol provides a greater oxidation stability to the long-chain oil relative to the oxidation stability of the oil alone.

18. The composition according to claim 17 further comprising at least one supplemental additive, wherein the at least one supplemental additive selected from the group consisting of kojic acid, malic acid, and ascorbic acid, wherein said tocopherol is present in an amount of from 0.01 to 5% by weight of said long-chain oil, wherein said tocopherol and said at least one supplemental additive in combination provide a greater oxidation stability to the tong-chain oil relative to the oxidation stability of the oil alone.

19. The emollient composition of claim 13 wherein said composition is used in cosmetic applications selected from the group consisting of creams, lotions, and liquid foundations; massage oils; pressed products, such as eye shadow, blush, and powder; molded products, such as lipstick, lip balm, foundation, blush, eye liner, eye shadow, mascara; and hair care products, such as leave in conditioners, relaxers, hair dyes.

20. A massage oil having improved slip properties comprising a long-chain oil of moringa, said long-chain oil has a methylene interrupted unsaturation of less tan 1%, where the long-chain oil of moringa has a slip value greater than that of castor oil, 7.0 as measured by a modified Cadicamo method.

21. The composition according to claim 20, wherein the long-chain oil is a derivative of the oil produced from *Moringa oleifera*.

22. The composition according to claim 20, further comprising at least one tocopherol, wherein said tocopherol provides a greater oxidation stability to the long-chain oil relative to the oxidation stability of the oil alone.

23. The composition according to claim 22 further comprising at least one supplemental additive, wherein the at least one supplemental additive selected from the group consisting of kojic acid, malic acid, and ascorbic acid, wherein said tocopherol is present in an amount of from 0.01 to 5% by weight of said long-chain oil, wherein said tocopherol and said at least one supplemental additive in combination provide a greater oxidation stability to the long-chain oil relative to the oxidation stability of the oil alone.

24. The composition according to claim 21, further comprising at least one tocopherol, wherein said tocopherol provides a greater oxidation stability to the long-chain oil relative to the oxidation stability of the oil alone.

25. The composition according to claim 24 further comprising at least one supplemental additive, wherein the at least one supplemental additive selected from the group consisting of kojic acid, italic acid, and ascorbic acid, wherein said tocopherol is present in an amount of from 0.01 to 5% by weight of said long-chain oil, wherein said tocopherol and said at least one supplemental additive in combination provide a greater oxidation stability to the long-chain oil relative to the oxidation stability of the oil alone.

* * * * *